(12) United States Patent
Liang et al.

(10) Patent No.: US 6,828,464 B2
(45) Date of Patent: Dec. 7, 2004

(54) PREPARATION OF CYCLOPENTENONES

(75) Inventors: Shelue Liang, Ludwigshafen (DE);
Rolf-Hartmuth Fischer, Heidelberg (DE); Sylvia Huber-Dirr, Zwingenberg (DE); Andrea Haunert, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/718,795

(22) Filed: Nov. 24, 2003

(65) Prior Publication Data
US 2004/0102655 A1 May 27, 2004

(30) Foreign Application Priority Data

Nov. 25, 2002 (DE) .......................... 102 54 853

(51) Int. Cl.$^7$ .............................. C07C 45/54
(52) U.S. Cl. ................ 568/346; 568/347; 568/355; 568/356
(58) Field of Search ................ 568/346, 347, 568/355, 356

(56) References Cited

U.S. PATENT DOCUMENTS

| 3,953,514 A | 4/1976 | Yamazaki et al. .......... 260/586 |
| 5,118,864 A | 6/1992 | Merger et al. .............. 568/356 |

FOREIGN PATENT DOCUMENTS

| DE | 0 297 447 A2 | 6/1988 |
| DE | 0 446 759 B1 | 5/1991 |
| EP | 475 386 | 8/1995 |

OTHER PUBLICATIONS

J.Molecular Catalysis, 8(1980) 107–117, Verkuijlen.
J.Org.Chem, 1983, 48 5364–5366, Nugent et al.

Primary Examiner—Samuel Barts
Assistant Examiner—Sikarl A. Witherspoon
(74) Attorney, Agent, or Firm—Keil & Weinkauf

(57) ABSTRACT

The present invention provides a process for preparing 2-cyclopentenones of the general formula:

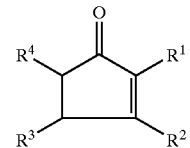

I where $R^1$ to $R^4$ are each hydrogen atoms or are alkyl or alkenyl radicals having from 1 to 12 carbon atoms, cycloalkyl or cycloalkenyl radicals having from 5 to 7 carbon atoms, aralkylene or aryl radicals, by converting hexenedioic acids and/or their esters of the general formulae

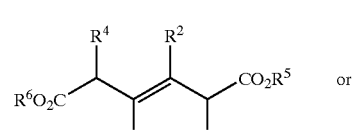

II or

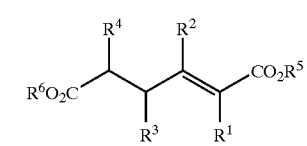

III where $R^1$ to $R^4$ are each as defined above and $R^5$ and $R^6$ are each hydrogen atoms or are alkyl radicals having from 1 to 12 carbon atoms, cycloalkyl radicals having 5 or 6 carbon atoms, aralkyl or aryl radicals, at temperatures of from 150 to 450° C., over solid, oxidic catalysts, wherein the catalysts on an oxidic support material comprise from 0.01 to 5% by weight of at least one alkali metal oxide.

6 Claims, No Drawings

PREPARATION OF CYCLOPENTENONES

The present invention relates to a process for preparing 2-cyclopentenones by converting 2- or 3-hexene-1,6-dicarboxylic acids or their esters in the presence of heterogeneous catalysts which consist of alkali metal oxides on catalyst supports.

The synthesis of 2-cyclopentenones by converting substituted or unsubstituted 2- or 3-hexene-1,6-dicarboxylic acids or their esters over solid oxidic catalysts at from 150° C. to 450° C. is disclosed by EP-A 297 447. The catalysts used are solid oxidic catalysts of main groups I to V, transition groups I to VIII of the Periodic Table of the Elements or oxides of the rare earth metals or mixtures of the oxides mentioned. Particular preference is given to carrying out the reaction in the gas phase using a fluidized catalyst bed. According to the four examples of EP-A 297 447, the catalyst used is more preferably γ-aluminum oxide or barium oxide-doped aluminum oxide.

The experiments in the four examples were conducted at 345° C./atmospheric pressure in the presence of steam, nitrogen as a carrier gas, and γ-aluminum oxide or γ-aluminum oxide/barium oxide fluidized bed catalysts, each for 6 hours. The highest yield when using γ-aluminum oxide was 51% (selectivity 65%, example 1), and when using γ-aluminum oxide/10% barium oxide 55% (selectivity 69%, example 4).

It is an object of the present invention to further improve the process for preparing cyclopentenones from 2- or 3-hexene-1,6-dicarboxylic acids or their esters, especially with regard to the cyclopentenone selectivity, by finding still better catalysts. A very high cyclopentenone yield should be combined with a high cyclopentenone selectivity, in order to have to recycle very little 2- or 3-hexene-1,6-dicarboxylic acids or their esters in the process. The catalysts should also have a very long on-stream time.

We have found that this object is achieved by a process for preparing 2-cyclopentenones of the general formula:

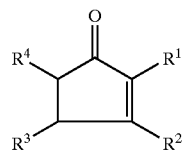

I where $R^1$ to $R^4$ are each hydrogen atoms or are alkyl or alkenyl radicals having from 1 to 12 carbon atoms, cycloalkyl or cycloalkenyl radicals having from 5 to 7 carbon atoms, aralkylene or aryl radicals, by converting hexenedioic acids and/or their esters of the general formulae

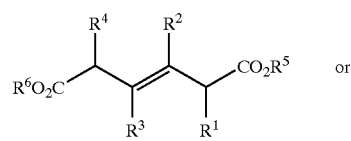

II or

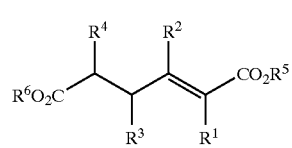

III where $R^1$ to $R^4$ are each as defined above and $R^5$ and $R^6$ are each hydrogen atoms or are alkyl radicals having from 1 to 12 carbon atoms, cycloalkyl radicals having 5 or 6 carbon atoms, aralkyl or aryl radicals, at temperatures of from 150 to 450° C., over solid, oxidic catalysts which, on an oxidic support material, comprise from 0.01 to 5% by weight, preferably from 0.1 to 3% by weight, more preferably from 0.3 to 2% by weight, of at least one alkali metal oxide. Percentages by weight are based in each case on the overall catalyst composed of active metal oxide and support material.

Useful alkali metal oxides are lithium oxide, sodium oxide, potassium oxide, rubidium oxide, and cesium oxide or mixtures thereof. Particular preference is given to sodium oxide and potassium oxide as the catalytically active composition.

Useful support materials are metal oxides of main groups II to V, transition groups I to VIII of the Periodic Table of the Elements, or oxides of the rare earth metals or mixtures thereof. Examples of such supports are magnesium oxide, calcium oxide, barium oxide, and also boron trioxide, aluminum oxide, silicon oxide, for example in the form of silica gel, kieselguhr or quartz, and also tin dioxide, bismuth oxide, copper oxide, zinc oxide, lanthanum oxide, titanium dioxide, zirconium dioxide, vanadium oxides, chromium oxides, molybdenum oxides, tungsten oxides, manganese oxides, iron oxides, cerium oxides, neodymium oxides, or mixtures of such oxides.

Preference is given to using aluminum oxide and/or silicon oxide as the support material.

The supported catalysts used in accordance with the invention can be prepared by processes known per se, for example by precipitating the catalytically active component from its salt solutions in the presence of the support material by adding an alkali metal hydroxide or carbonate solutions. The particular hydroxides, oxide hydrates, basic salts or carbonates are precipitated in this way.

The precipitates are subsequently dried and converted by calcining, generally at from 300 to 1300° C., preferably from 400 to 1200° C., to the corresponding oxides, mixed oxides and/or mixed-valency oxides.

In addition to the abovementioned precipitation catalysts which can be used as supported catalysts, also suitable are supported catalysts in which the catalytically active components have been applied to the support material in another way.

For example, the catalytically active components can be applied by impregnating with solutions or suspensions of the salts or oxides of the appropriate elements and drying.

The supported catalysts can also be prepared by mixing the support with an alkali metal salt and water, kneading and extruding the mixture and subsequently drying and calcining.

The catalytically active components can also be applied to the support by impregnating the support with solutions of salts which readily decompose thermally and heating the support treated in this way to temperatures of from 300 to 600° C., which thermally decomposes the adsorbent metal compounds.

Salts which readily decompose thermally are, for example, nitrates and complexes which readily decompose thermally, such as carbonyl or hydrido complexes of the catalytically active metals. Preference is given to carrying out the thermal decomposition in a protective gas atmosphere. Suitable protective gases are, for example, nitrogen, carbon dioxide, hydrogen or noble gases.

The catalytically active component can also be deposited on the support material by vapor deposition or flame spraying.

The reaction according to the invention can be illustrated, for example, for the conversion of dimethyl 3-hexene-1,6-di-carboxylate to 2-cyclopentenone by the following reaction equation:

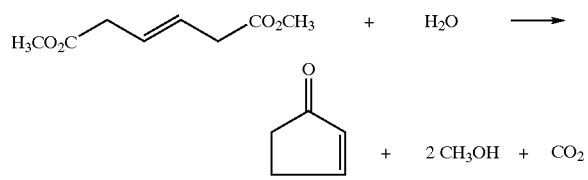

Useful starting materials of the formulae II and III include 3-hexene-1,6-dicarboxylic acid or 2-hexene-1,6-dioic acid, each of which may optionally be substituted by the $R^1$ to $R^4$ radicals. The $R^1$ to $R^4$ radicals may be alkyl or alkenyl radicals having from 1 to 12 carbon atoms, such as methyl, ethyl, propyl, isopropyl, butyl, isobutyl, tert-butyl, hexyl, nonyl, allyl, hexenyl or nonenyl radicals, cycloalkyl or cycloalkenyl radicals having from 5 to 7 carbon atoms, such as cyclohexyl, cyclopentyl, 2-cyclohexenyl or 2-cyclopentenyl radicals, aralkyl or aryl radicals, such as phenyl or benzyl radicals. The esters of the formulae II and III are aliphatic, cycloaliphatic, araliphatic or aromatic mono- or diesters of the dicarboxylic acids mentioned. Useful $R^5$ and $R^6$ radicals are, for example, methyl, ethyl, propyl, isopropyl, tert-butyl, hexyl, nonyl, dodecyl, cyclopentyl, cyclohexyl, phenyl or benzyl radicals.

The following starting materials, for example, can be used:
3-hexene-1,6-dioic acid, 2-hexene-1,6-dioic acid, 2-methyl-3-hexene-1,6-dioic acid, 2,5-dimethyl-3-hexene-1,6-dioic acid, 3,4-dimethyl-3-hexene-1,6-dioic acid, 2-allyl-3-hexene-1,6-dioic acid, 3-cyclohexyl-2-hexene-1,6-dioic acid, 3-(2-cyclopentyl)-3-hexene-1,6-dioic acid, 3-phenyl-3-hexene-1,6-dioic acid and 2-benzyl-3-hexene-1,6-dioic acid, dimethyl 3-hexene-1,6-dioate, dimethyl 2-hexene-1,6-dioate, monomethyl 3-hexene-1,6-dioate, diethyl 3-hexene-1,6-dioate, dibutyl 2-hexene-1,6-dioate, dicyclohexyl 3-hexene-1,6-dioate, dibenzyl 3-hexene-1,6-dioate, dimethyl 2-methyl-3-hexene-1,6-dioate, dimethyl 2,5-dimethyl-3-hexene-1,6-dioate, dimethyl 3,4-dimethyl-3-hexene-1,6-dioate, dimethyl 2-allyl-3-hexene-1,6-dioate, diethyl 3-cyclohexyl-2-hexene-1,6-dioate, dimethyl 3-(2-cyclopentenyl)-3-hexene-1,6-dioate, diethyl 3-phenyl-3-hexene-1,6-dioate or dimethyl 2-benzyl-3-hexene-1,6-dioate. The conversion of the esters is of particular industrial interest.

Although it is possible to carry out the reaction according to the invention without addition of water, the addition of water achieves a remarkable increase of selectivity and on-stream time. The molar ratio of starting material II or III to water in this context is advantageously from 1:0.01 to 1:20, in particular from 1:0.5 to 1:10.

The conversion can be carried out in the gas phase or in the liquid phase, optionally also with the use of diluents. Particular preference is given to carrying out the reaction in the gas phase as a fixed bed reaction with fixed bed catalysts.

The conversion takes place at from 200 to 450° C., preferably from 250 to 430° C., in particular from 300 to 420° C. In general, the reaction is carried out under atmospheric pressure. However, it is also possible to employ a slightly reduced or slightly increased pressure, for example up to 20 bar. The catalyst hourly space velocity is generally from 0.01 to 40 g, preferably from 0.1 to 20 g, of starting material of the formula II and/or III per gram of catalyst and hour.

The conversion in the liquid phase is carried out, for example, in such a way that a mixture of the starting compound and optionally water is heated to the desired reaction temperature in the presence of a suspended fixed bed catalyst. On expiry of the necessary reaction time, the reaction mixture is cooled and the catalyst removed, for example by filtration. The reaction mixture is subsequently fractionally distilled to recover the ketone and/or the unconverted starting material.

In a preferred embodiment of the process according to the invention in the gas phase, for example, a mixture of the starting material of the formula II and/or III and water is initially evaporated and then passed at the desired reaction temperature in gaseous form over a fixed bed catalyst, optionally together with an inert gas such as nitrogen, carbon dioxide or argon. In the case of a fixed bed arrangement, preference is given to the trickle method in which the gas and liquid are conducted from top to bottom through the catalytic fixed bed. The reaction effluent is condensed by means of a suitable cooling apparatus and subsequently worked up by fractional distillation. Unconverted starting material can be recycled.

The starting materials required for the process according to the invention can be prepared starting from 1,4-bicyano-2- or 1,4-dicyano-3-butenes by hydrolysis or reaction with alcohols and hydrochloric acid (Pinner reaction), by metathesis of alkenecarboxylic esters (see, for example, J. of Molecular Catalysis 8 (1980), p. 107 to 11[lacuna]) or by catalytic dimerization of acrylic esters, for example with Pd catalysts, as described in J. Org. Chem. 48 (1983), p. 5364 to 5366, or Rh catalysts (see also EP-A 475 386), not only easily in good yields, but also with a substitution pattern which can be varied within wide limits. In this context, particular preference is given to the dimerization of acrylic esters.

EP-A 269 042 discloses the conversion of methyl 2- and 3-pentenoates at from 130 to 135° C. in the presence of strong bases such as sodium methoxide, sodium amide or sodium hydride to give mixtures of dimethyl 2-propenylidene- and 2-(1-propenyl)-3-ethylglutarate, i.e. dimeric pentenoic esters. A similar dimerization was to be expected in the conversion of 2- and 3-hexenedicarboxylic diesters at distinctly higher temperatures and using alkali metal oxides, i.e. likewise strong bases. It was therefore surprising that, in example 1, cyclopentenone yields of 85% are achieved at selectivities of 91%.

The 2-cyclopentenones obtainable by the process according to the invention are valuable intermediates. The α,β-unsaturated ketone system in the 2-cyclopentenones enables a multitude of addition reactions of the Michael or Diels-Alder type. 2-Cyclopentenones are therefore valuable and versatile starting compounds for the synthesis of five-membered rings.

The process according to the invention is illustrated by the examples which follow.

EXAMPLES

Example 1

Preparation of the Cyclization Catalyst A (1% of $K_2O/Al_2O_3$)

3 kg of $Al_2O_3$ were kneaded with 0.05 kg of potassium carbonate and 2.8 kg of water. The thoroughly mixed composition was shaped to 4 mm extrudates and dried at 120° C. The dried extrudates were calcined at 1200° C.

Example 2

Cyclization of Dimethyl 3-hexene-1,6-dioate to 2-cyclopentenone

In an electrically heated gas phase reactor, 80 ml of catalyst A were covered with 20 ml of quartz rings as the evaporator zone. The apparatus was operated by the trickle method. 0.008 kg of dimethyl 3-hexene-1,6-dioate and 0.004 ml of water were evaporated per hour and passed over catalyst A with 20 l of nitrogen at 400° C. The catalyst hourly space velocity was 0.1 kg of dimethyl 2-hexene-1, 6-dioate/1of catalyst×hour.

The gaseous reaction effluent was condensed with cooling and analyzed with gas chromatography. The 2-cyclopentenone yield was 85%, the selectivity 91%.

We claim:

1. A process for preparing 2-cyclopentenones of the general formula:

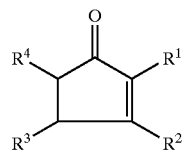

I where $R^1$ to $R^4$ are each hydrogen atoms or are alkyl or alkenyl radicals having from 1 to 12 carbon atoms, cycloalkyl or cycloalkenyl radicals having from 5 to 7 carbon atoms, aralkylene or aryl radicals, by converting hexenedioic acids and/or their esters of the general formulae

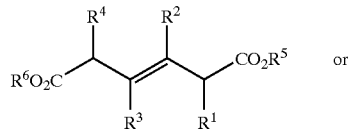

II or

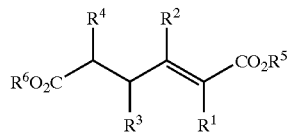

III where $R^1$ to $R^4$ are each as defined above and $R^5$ and $R^6$ are each hydrogen atoms or are alkyl radicals having from 1 to 12 carbon atoms, cycloalkyl radicals having 5 or 6 carbon atoms, aralkyl or aryl radicals, at temperatures of from 150 to 450° C., over solid, oxidic catalysts, wherein the catalysts on an oxidic support material comprise from 0.01 to 5% by weight of at least one alkali metal oxide.

2. A process as claimed in claim 1, wherein the support material used is a metal oxide of main groups II to V, transition groups I to VIII of the Periodic Table of the Elements, an oxide of the rare earth metals or a mixture thereof.

3. A process as claimed in claim 1, wherein the support material used is aluminum oxide and/or silicon oxide.

4. A process as claimed in claim 1, wherein sodium oxide and/or potassium oxide are used.

5. A process as claimed in claim 1, wherein the reaction is carried out in a fixed bed.

6. A process as claimed in claim 1, wherein the starting materials of the general formulae II and III are prepared by dimerizing acrylic esters.

* * * * *